United States Patent [19]
Kosslak et al.

[11] Patent Number: 5,229,113
[45] Date of Patent: Jul. 20, 1993

[54] BRADYRHIZOBIUM JAPONICUM NODULATION INDUCING FACTOR

[75] Inventors: Renee Kosslak; Roger Bookland; Edward R. Appelbaum, all of Madison, Wis.

[73] Assignee: Lubrizol Genetics, Inc., Wickliffe, Ohio

[21] Appl. No.: 393,081

[22] Filed: Aug. 9, 1989

Related U.S. Application Data

[63] Continuation of Ser. No. 35,516, Apr. 7, 1987, abandoned.

[51] Int. Cl.$^5$ .................. A01N 63/00; A01N 43/00; C12R 1/41; C12N 1/00; C05F 11/08; A01C 1/06
[52] U.S. Cl. .................. 424/93 A; 435/252.2; 435/878; 71/7; 47/57.6; 47/DIG. 9; 47/DIG. 10; 424/93 D; 504/117
[58] Field of Search .................. 71/7, 88; 47/58, 57.6, 47/DIG. 9, DIG. 10; 424/93; 435/252.2, 878

[56] References Cited

U.S. PATENT DOCUMENTS 4,232,122 11/1980 Zilliken .................. 435/52

FOREIGN PATENT DOCUMENTS 0236553 9/1987 European Pat. Off. .

OTHER PUBLICATIONS

Mentzer, C., 1963, Chem. Abstr., 58:#6655c.
Porter et al., 1986, Env. Exper. Bot., 26(1):65-73.
D'Arcy-Lameta, A., 1986, Plant Soil, 92(1):113-123.
Sansei Pharmaceutical Co., 1985, Chem. Abstr., 103(16):#128809b.
Farukosu, I., 1984, Chem. Abstr., 100(16):#126730q.
d'Arcy-Lameta et al., 1987, Plant and Soil, 101(2):267-272.
Firmin et al., 1986, Nature, 324:90-92.
Djordjevic et al., 1987, EMBO J., 6(5):1173-1179.
Mulligan et al., 1985, Proc. Natl. Acad. Sci., 82:6609-6613.
Lamb et al., 1986, Mol. Gen. Genet., 202:512-517.
Molina et al., 1967, Can. J. Microbiol., 13:819-827.
Bhagwat et al., 1982, Appl. Env. Microbiol., 43:800-805.
Cunningham et al., (1991), Appl. Envir. Microbiol., 57:1886-1892.
Kosslak et al., (1990), Appl. Environ. Microbiol., 56:1333-1341.
Peters et al., (1986), Science, 233:977-980.
Redmond et al., (1986), Nature, 323:632-635.
Zaat et al., (1987), J. Bacteriol., 169:198-204.
Rossen et al., (1985), EMBO J., 4:3369-3373.
Innes et al., (1985), Mol. Gen. Genet., 201:426-432.
Halverson and Stacy, (1984), Plant Physiol., 74:84-89.
Halverson and Stacy, (1985), Plant Physiol., 77:621-624.
Nieuwkoop et al., (1987), 87th Ann. Meeting of the American Soc. for Microbiology, Atlanta, Ga., Mar. 1-6, Meeting Abstracts, 87(0), p. 210.

*Primary Examiner*—David T. Fox
*Attorney, Agent, or Firm*—Greenlee & Assoc.

[57] ABSTRACT

The chemical compounds that induce expression of nodulation genes of *Bradyrhizobium japonicum* strains have been identified. The isoflavones daidzein and genistein were identified as soybean exudate components that induce nod-genes. Other isoflavones, including 7-hydroxyisoflavone, 5,7-dihydroxyisoflavone, biochanin A, formononetin and prunetin, were also found to act as inducers. In addition, several flavonoid compounds including 4',7-dihydroxyflavone, apigenin, kaempferol and coumestrol, were also found to act as inducers. Nodulation inducing compositions and a method for selectively activating the expression of a gene under the control of a soybean exudate inducible promoter in *B. japonicum* in response to these inducer molecules are described. In addition, soybean inoculating compositions containing the nod-gene inducers and inoculating methods employing these compositions are described.

20 Claims, 4 Drawing Sheets

POSITIONS AND ORIENTATIONS OF Nod GENES IN B. japonicum

FIG. 1

POSITIONS AND ORIENTATIONS OF Nod GENES IN B. japonicum

FIG. 2  CONSTRUCTION AND STRUCTURES OF pEA2-21 AND pEA4-10

STRUCTURE OF Bradyrhizobium japonium nod GENE INDUCERS

Daidzein

Genistein 7-hydroxyisoflavone 5,7-dihydroxyisoflavone biochanin A

Prunetin

Formononetin 7,4'-dihydroxyflavone

Apigenin

Coumestrol

FIG. 3

BRADYRHIZOBIUM JAPONICUM NODULATION INDUCING FACTOR

This application is a continuation of application Ser. No. 07/035,516, filed Apr. 7, 1987, now abandoned.

FIELD OF THE INVENTION

The present invention relates in general to the field of legume-Rhizobium symbiosis and in particular to the identification of flavonoid compounds which stimulate expression of the nodulation genes of *Bradyrhizobium japonicum* strains which nodulate the agronomically important legume, soybean. These compounds are useful in general for selective control of gene expression and in particular as components of improved soybean inoculating compositions.

BACKGROUND OF THE INVENTION

Genera of soil bacteria that are members of the family Rhizobiaceae, are capable of infecting plants and inducing highly differentiated structures, root nodules, within which atmospheric nitrogen is reduced to ammonia by the bacteria. The host plant, most often of the family *Leguminose*, utilizes the ammonia as a source of nitrogen. Nodulating bacteria are classified in two taxonomically distinct groups, the fast-growing Rhizobium species and the slow-growing Bradyrhizobium species (Jordan, D. C. (1982) Int. J. Syst. Bacteriol. 32:136). Bradyrhizobium species include the commercially important soybean nodulating strains *B. japonicum* (i.e., strains USDA 110 and 123), promiscuous rhizobia of the cowpea group, and *B. parasponia* (formerly *Parasponia Rhizobium*) which nodulates the non-legume Parasponia, as well as a number of tropical legumes including cowpea and siratro. *Bradyrhizobium japonicum* strains have a narrow host range for nodulation generally limited to soybean, Glycine max. Fast-growing Rhizobium include, among others, *Rhizobium trifolii, R. meliloti* and *R. leguminosarum*, which nodulate clover, alfalfa and pea, respectively. These Rhizobium species also generally display narrow plant host range for nodulation. *Rhizobium fredii*, formerly *R. japonicum*, have a broader host range for nodulation including Glycine max cv. Peking, but not commercially useful soybean cultivars.

Nodulation and the development of effective symbiosis is a complex process requiring both bacterial and plant genes. Several recent reviews of the genetics of the Rhizobium-legume interaction are found in Broughton, W. J., ed. (1982) *Nitrogen Fixation*, Volumes 2 and 3 (Clarendon Press, Oxford); Puhler, A. ed. (1983) *Molecular Genetics of the Bacteria-Plant Interaction* (Springer-Verlag, Berlin); Szalay, A. A. and Leglocki, R. P., eds. (1985) *Advances in Molecular Genetics of the Bacteria-Plant Interaction* (Cornell University Publishers, Ithaca, N.Y.); Long. S. R. (1984) in *Plant Microbe Interactions* Volume 1, Kosuge, T. and Nester, E. W., eds. (MacMillan, New York) pp. 265-306; and Verma, D. P. S. and Long, S. L. (1983) International Review of Cytology (Suppl. 14), Jeon, K. W. (ed.), (Academic Press, N.Y.) p. 211-245.

In Rhizobium species genes required for nodulation and nitrogen fixation are located on large Sym plasmids. Although the process of recognition, infection and nodule development is complex, it appears that at least for the fast-growing rhizobia relatively few bacterial genes are directly involved, and these are closely linked on the Sym plasmid. See Schofield et al. (1984) Plant Mol. Biol. 3:3-11; (Downie et al (1983) Mol. Gen. Genet. 190:350-365; and Kodorosi et al. (1984) Mol. Gen. Genet. 193:445-452). In contrast, no Sym plasmids have been associated with *B. japonicum* strains. The nitrogenase and nodulation genes of these organisms are believed to be encoded on the bacterial chromosome.

Nodulation genes are those genes associated with non-nodulation and delayed nodulation phenotypes. Several nodulation genes designated nodABC and D, which are functionally and structurally conserved among the fast-growing Rhizobium, have been identified by hybridization studies and cross-species complementation experiments. These genes are designated the common nod genes. Recently it has been reported that *B. parasponia* (Marvel et al. (1985) Proc. Natl. Acad. Sci. U.S.A. 82:5841-5845) and *B. japonicum* (Russel et al. (1985) J. Bacteriol. 164:1301-1308) contain nodulation genes which can functionally complement mutations in fast-growing Rhizobium and which show considerable structural homology to nodulation gene regions of *R. meliloti* and *R. leguminosarum*. Structural conservation between Rhizobium and Bradyrhizobium extends to other nodulation genes, nodI, J. Stacy et al. (1987) in *Molecular Genetics of Plant-Microbe Interactions*, Verma and Brisson (eds.) Martinus Nijhoff Publishers, Dordrecht, Netherlands, pp. 197-201, have recently reviewed the genetics of nodulation in *B. japonicum*.

In Rhizobium strains the common nod region, nodA, B and C genes are grouped sequentially and are coordinately transcribed as a single transcriptional unit. In some stranis, nodI and J are also reported to be part of this operon. The nodD gene is transcribed divergently from the nodABC(IJ) operon (Egelhoff et al. (1985) DNA 4:241-248; Jacobs et al. (1985) J. Bacteriol. 162:469-476; Rosen et al. (1984) Nucl. Acids Res. 12:9497-9508; and Torok et al. (1984) Nucl. Acids Res. 12:9509-9524). Divergent promoters for the nodABC operon and nodD are presumed to be located in the region between nodD and nodA.

Some Rhizobium strains contain more than one nodD-like gene. The presence of multiple nodD-like genes was first reported in *R. fredii* USDA 191 ((Appelbaum et al. (1985) in *Nitrogen Fixation Research Progress*, Marginus Nijhoff Publishers, Dordrecht, Netherlands, pp. 101-107) and subsequently in *R. meliloti* and other rhizobia (Gottfert et al. (1986) J. Mol. Biol. 191:411-420). Only one nodD gene has been reported in *R. trifolii* and *R. leguminosarum*. The presence of multiple nodD-like genes has not been reported in *B. japonicum*.

The functions of the multiple nodD like genes in the nodulation process or its regulation are not yet understood.

Regulation of the nodulation genes in Rhizobium species has been investigated. Only one nodulation gene, nodD, is reported to be constitutively expressed. Expression of the other nodulation genes including nodABCEFGHI and J requires the presence of appropriate exudate and a functional of nodD (Mulligan and Long (1985) Proc. Natl. Acad. Sci. U.S.A. 82:6609-6613; Rossen et al. (1985) EMBO J. 4:3369-3373; Innes et al. (1985) Mol. Gen. Genet. 201:426-432. Conserved DNA sequence elements are found within the promoter regions of the nodABC(IJ) operon in *R trifolii, R. meliloti, R. leguminosarum*, and in the nodEF operon and nodH in *R trifolii*. (Scott et al.

(1985); Rolfe et al. (1985); Kondorosi et al. (1985) *Nitrogen Fixation Research Progress,* Evans et al. (eds) Martinus Nighoff, Dordrecth, The Netherlands p. 73-75). These consensus sequences are associated with exudate-inducible expression of the nod genes and their presence in various Rhizobium suggest a conserved regulatory mechanism.

The presence of nod-box conserved sequences in nodulation promoter regions in *B. parasponia* (Scott (1986) Nucleic Acids Res. 14:2905-2919) and *B. japonicum* (Appelbaum et al. (1986) U.S. patent application Ser. No. 875,297, filed Jun. 17, 1986; and Stacy et al., 1987) has been reported. The presence of these regulatory sequences strongly suggests conservation of nodulation gene regulation in Bradyrhizobium and Rhizobium.

Nodulation genes of Bradyrhizobium strains as their analogues in Rhizobium strains affect the early stages of nodule formation including host-bacterium recognition, infection and nodule development. Wild type strains of Bradyrhizobium species display some variation in these early nodulation steps which is reflected in differences in relative rates of initiation of nodulation and ultimately in differences in competitiveness between strains for nodula occupancy. For example, *B. japonicum* USDA 123 is believed to be more competitive for nodulation than *B. japonicum* USDA 110. Strains which initiate infection and nodules earlier will occupy a greater portion of the nodules on a given plant. Improving the competitiveness of a specific Bradyrhizobium is an important part of the development of improved inocula for legumes. A more effective Bradyrhizobium strain, which would likely constitute an improved inoculum, must be able to out-compete the indigenous rhizobia population for nodule occupancy in order for their improved qualities to impact on the inoculated legume. An inoculating composition and/or an inoculating method which would improve competitiveness of a selected inoculant strain is therefore of significant commercial importance.

The establishment of nitrogen-fixing nodules is a multistage process involving coordinated morphological changes in both bacterium and plant requiring precise gene regulation. It has been suggested that an exchange of signals between plant and bacterium is requisite for mutual recognition and coordination of the steps of infection and nodulation development (Nutman, P. S. (1965) in *Ecology of Soil Borne Pathogens,* eds. F. K. Baker and W. C. Snyder, University of California Press, Berkeley, pp. 231-147; Bauer, W. D. (1981) Ann. Rev. Plant Phys. 32:407-449; and Schmidt, E. E. (1979) Ann. Rev. Microbiol. 33:355-376). The regulation of nodulation genes of rhizobia by chemical factors excreted by legumes in exudates is a specific demonstration of communication between host and symbiont.

Legume exudates have been previously linked to both simulation (Thornton (1929) Proc. Royal Soc. B 164:481; Valera and Alexander (1965) J. Bacteriol. 89:1134-1139; Peters and Alexander (1966) Soil Science 102:380-387) and inhibition (Turner (1955) Annals Botany 19:149-160; and Nutman (1953) Annals Botany 17:95-126) of nodulation by rhizobia.

Turner (1955) reported that addition of activated charcoal to rooting medium of clover plants led to an increased rate of nodule initiation. Activated charcoal was demonstrated to remove by adsorption an unidentified inhibitory substance secreted by clover roots. Nutman (1953) reported that clover roots excreted a substance inhibitory to nodulation. The substance was not identified but was found to be associated with the stage of nodulation on the plant. In both cases, it was suggested that both stimulatory and inhibitory factors were present in the root exudate.

Valera and Alexander (1965) and Peters and Alexander (1966) reported a nodulation enhancing factor in legume exudates that was dialyzable, water soluble and thermostable. This factor was replaceable by coconut water. More recently, Baghwat and Thomas (1982) Applied Environ. Microbiol. 43:800-805 described a stimulatory factor from legume exudates that was thermostable, was high molecular weight (about $2 \times 10^5$) and was composed of protein and neutral hexoses. This factor was associated with elimination of nodulation delay in a certain cowpea Rhizobium strain. Halverson and Stacey (1984) Plant Physiol. 74:84-89; and (1985) Plant Physiol. 77:621-624 reported an exudate factor having a similar affect on nodulation initiation in *B. japonicum* USDA 110 mutants. In contrast to Baghwat and Thomas (1982), this stimulator of nodulation was described as a heat and trypsin sensitive protein, a galactose-specific lectin.

In addition to factors present in legume exudate, diverse chemicals have been identified as stimulators or inhibitors of nodulation. Reported stimulators of nodulation include inositol, indole, 2-phenol-n-butyric acid, D-leucine, barbituric acid, pyridine-3-sulfonate and quercetin (Molina and Alexander (1967) Can. J. Microbiol. 13:819-827; and Weir (1960) Phyton 15:109-118).

The specific components of legume exudates that act to induce nodulation gene expression in several species of Rhizobium have recently been identified. In addition, a number of compounds related in structure to the inducer components of exudate have also been identified as inducers of *Rhizobium* nod genes.

Peters et al. (1986) Science 233:977-980 identified luteolin (3',4',5,7-tetrahydroxyflavone) as the component of alfalfa exudates that induces nodABC expression in *R. Meliloti.* Nod gene induction was assayed as $\beta$-galactosidase expressed from a lacZ gene which had been fused to the nodC gene of *R. meliloti.* In this gene fusion, the lacZ structural gene was placed under the regulatory control of the nodABC promoter and its associated nod-box regulatory sequence. A number of chemical compounds structurally related to luteolin were assayed for nod-gene induction in this system including several flavones, flavanones and flavanols. Of those compounds tested, only apigenin was found to induce the *R. meliloti* nod gene. Apigenin was found to be a much weaker inducer than luteolin.

Using similar nod-lacZ fusions in several nod genes, Redmond et al. (1986) Nature 323:632-635 reported the identification of three clover exudate components that induced expression of *R. trifolii* nod genes: 4',7-dihydroxyflavone (DHF), geraldone (3'-methoxy DHF) and 4'-hydroxy-7-methoxyflavone. In related work, Rolfe et al. (1986) U.S. patent application Ser. No. 844,870, filed Mar. 27, 1986, now abandoned, a number of substituted flavones, flavanols and flavanones were identified as *R. trifolii* nod gene inducers including luteolin and naringenin. Induction activity was reported to be confined to molecules having the flavone ring structure, in particular the isoflavones, daidzein and formononetin and coumestrol were inactive for *R. trifolii* nod gene induction.

Two of the nodulation gene inducers of *R. leguminosarum* from pea exudate were identified as eriodictyol (3',4', 5,7-tetrahydroxyflavanone) and apigenin-7-O-glucoside by Firmin et al. (1986) Nature 324:90-92. Apigenin, hesperitin and naringenin, in addition to other flavones and flavanones were also found to be active as inducers. The isoflavones daidzein, genistein and kaempferol were reported to be antagonists which strongly inhibited the activation of nod genes by inducers.

Zaat et al. (1987) J. Bacteriol. 169:198-204 characterized a R. leguminosarum nodulation gene inducer from Vicia sativa exudate as "flavonoid in nature, most likely a flavanone." Although the exudate component was not identified, naringenin, eridodictyol, apigenin and luteolin were reported to be strong nod inducers; 7-hydroxyflavone, a somewhat weaker inducer, and chrysin and kaempferol were weak or poor inducers. Among others, the isoflavones daidzein, genistein and prunetin were reported to be inactive.

The present work reports the identification of nodulation gene inducer compounds which activate expression of nodulation genes of Bradyrhizobium japonicum. These inducer compounds are useful in general for selective induction of genes placed under the regulatory control of B. japonicum soybean exudate inducible promoters and as components of soybean inoculation compositions.

SUMMARY OF THE INVENTION

The present work describes the identification of chemical compounds that induce expression of nodulation genes of Bradyrhizobium japonicum.

Genetic constructs in which a reporter gene, i.e. the lacZ gene is fused to a soybean exudate inducible nodulation gene, were prepared. Expression of the lacZ gene in B. japonicum strains containing these constructions reflects nod gene induction. So in combination with standard methods for assaying $\beta$-galactosidase activity, bacteria containing such constructs constitute an assay system for identifying compounds that induce B. japonicum nodulation genes.

Using such an assay, the isoflavones daidzein, genistein, 7-hydroxyisoflavone, 5,7-dihydroxyisoflavone, biochanin A and formononetin. The flavones 4',7-dihydroxyflavone (DHF) and apigenin; and the flavonol kaempferol and coumestrol were identified as B. japonicum nodulation gene inducing compounds. Of these, formononetin, kaempferol and coumestrol were characterized as weak inducers. Daidzein and genistein were found to be nod-gene inducers present in soybean exudates. The nodulation gene induction assay can also be employed to determine the concentration range over which a particular inducer will be effective.

It is a principal object of this invention to identify molecules which stimulate nodulation gene expression in strains of B. japonicum.

It is also an object of this invention to describe the use of these nodulation gene inducer compounds as components of nodulation inducing compositions and soybean inoculating compositions. Inducing compositions contain as an essential component an amount of an inducer compound effective for inducing expression of a nodulation gene of a strain of B. japonicum. Soybean inoculating compositions contain as essential ingredients a strain of Bradyrhizobium japonicum and an inducer compound which is present at a concentration effective for nodulation gene induction. The inoculant B. japonicum combined with or in such compositions are more competitive for infection and nodulation of soybean, compared to bacterial populations not exposed to the inducer.

It is another object of the invention to provide an improved method of inoculating soybeans employing nodulation inducing or soybean inoculating compositions of the present invention.

Daidzein, genistein, 7-hydroxyisoflavone, 5,7-dihydroxyisoflavone, biochanin A, 4',7-dihydroxyflavone and apigenin are the inducer compounds most preferred for use in the compositions of the present invention. Genistein is effective for nodulation gene induction at concentrations above about 0.1 $\mu$M. Daidzein and apigenin are effective for nodulation gene induction at concentrations above 0.1–0.25 $\mu$M. DHF is effective for nodulation gene induction at concentrations above 0.25–0.5 $\mu$M. The upper limit of the effective concentration is determined by toxicity of the inducer molecule toward B. japonicum or, if applicable, by the solubility limit of the inducer in the carrier chosen. Carriers suitable for use in nodulation inducing compositions and soybean inoculating compositions must be non-toxic to B. japonicum and must be substantially free of components that inhibit bacterial gene expression, particularly any components that specifically inhibit the action of the nodulation gene inducer compounds.

It is a further object of this invention to provide a method of selectively expressing in a strain of B. japonicum a gene which contains a soybean exudate-inducible promoter and a structural gene placed under the regulatory control of that promoter. Selective expression of such genes are obtained by contacting a culture of B. japonicum containing the gene with an effective amount of a nodulation gene inducer compound. Effective concentrations of inducers are as described for nodulation inducing and soybean inoculating compositions.

Another object of this invention is to provide recombinant vectors which contain Bradyrhizobium japonicum nod gene-lacZ fusions, which are useful in nodulation inducing assays. Such assays can be employed to identify additional B. Japonicum nodulation gene inducer compounds as well as to identify antagonists which inhibit their action and to determine effective concentration ranges for their use. The recombinant vectors preferred for use in the assays of the present invention are pEA2-21 and pEA4-10.

DETAILED DESCRIPTION OF THE INVENTION

Figure 1:
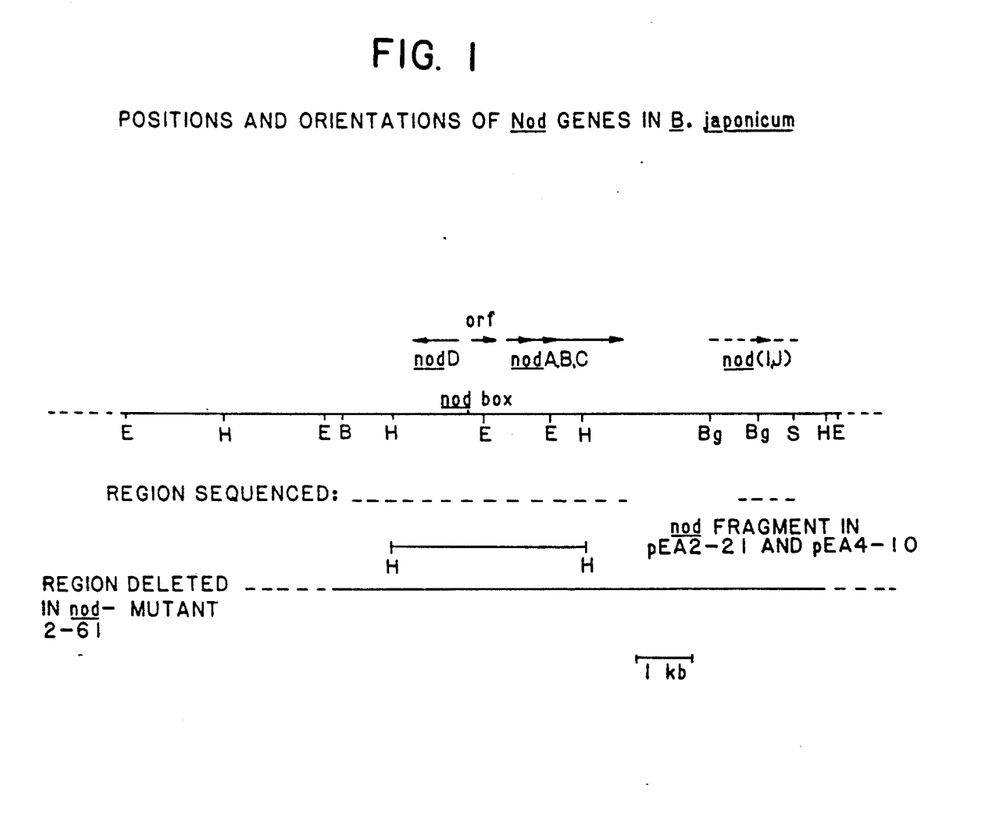
FIG. 1 is a restriction map of the nod gene region of Bradyrhizobium japonicum including nodD, orf and nodABC. A portion of this region has been sequenced as indicated. The nod region included in the 4.3 HindIII fragment used in the preparation of nodC-lacZ fusions is shown. The region deleted in the B. japonicum USDA 123 nod− mutant is indicated.

A restriction map of the cloned nod region of *B. japonicum* USDA 123 is shown in FIG. 1. The locations and orientations of the indicated nod genes have been confirmed by DNA sequence analysis. The nodA, B, C and D genes are structurally similar to and organized in a similar manner to the common nod genes of Rhizobium species. The nodA-nodD intergenic region contains a sequence element, termed the nod-box, which has been associated with legume exudate-inducible genes in Rhizobium. The nodA-nodD intergenic region presumably contains promoter and regulatory sequences (nod-box included) which control expression of nodD and the nodABC operon. The nod region of *B. japonicum* is distinct from analogous Rhizobium regions in that an open reading frame (ORF), possibly characteristic of Bradyrhizobium species is located upstream of nodA. The function, if any, of ORF in nodulation is unknown.

Figure 2:
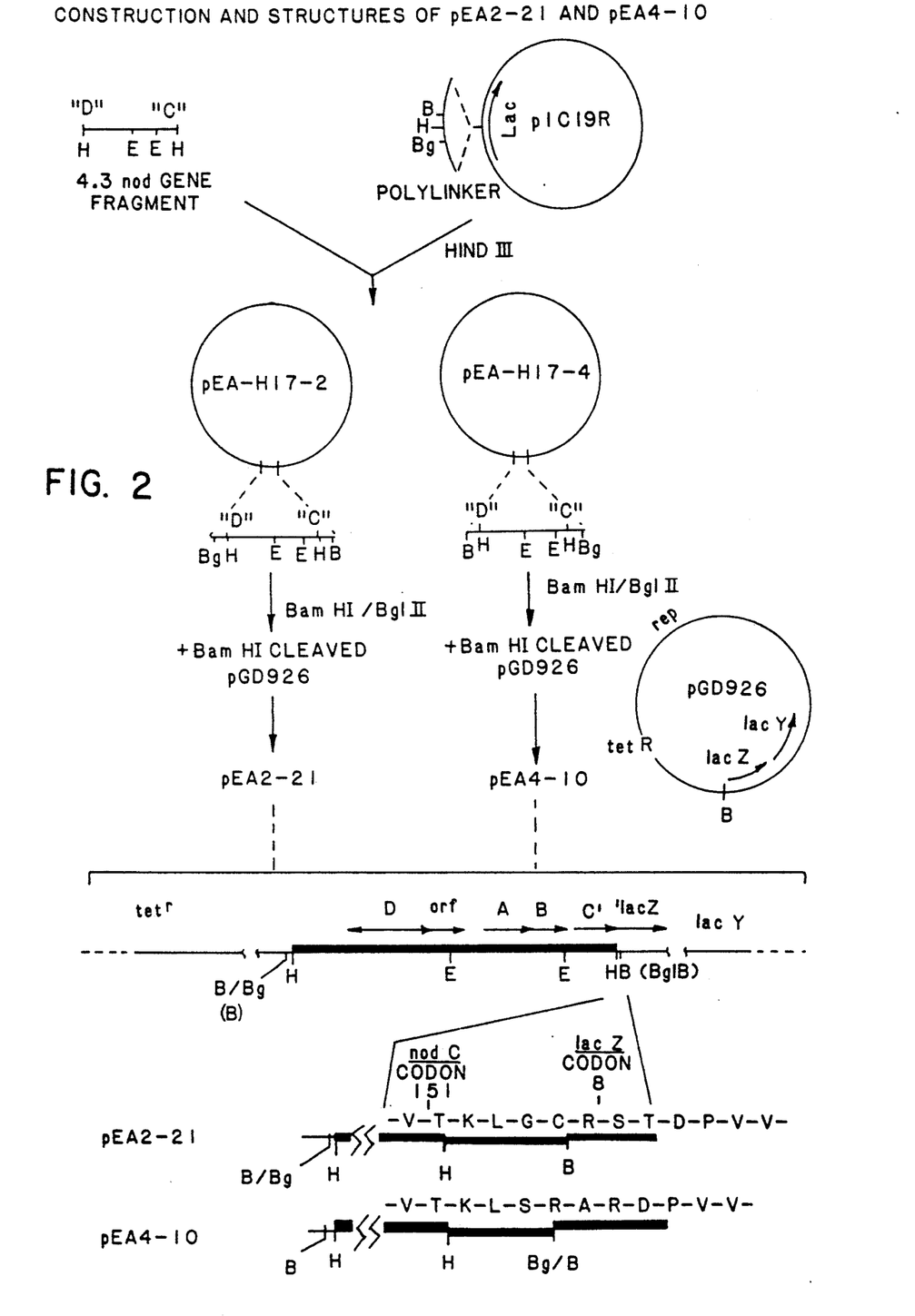
FIG. 2 is a schematic diagram of the construction of the nodC-lacZ fusion plasmids pEA2-21 and pEA4-10 which are described in Example 1. The structure and amino acid sequence at the nodC-lacZ fusion site is provided for both pEA2-21 and pEA4-10.

In order to study nodulation gene regulation and expression in *B. japonicum*, a lacZ gene fusion into the nodABC operon was constructed. The lacZ gene was placed under the regulatory control of the promoter and regulatory sequences of the nodABC operon so that expression of the lacZ, measured as β-galactosidase enzyme activity, reflected nod gene expression. Two recombinant vectors, pEA2-21 and pEA4-10, were constructed as shown in FIG. 2. Both contain the nodD, nod-box, ORF, nodA, B and part of nodC to which the lacZ gene is fused, and are the same except for the orientation of the *B. japonicum* DNA to flanking restriction sites and the DNA sequence at the fusion site (FIG. 2). In all inducer assays, pEA2-21 and pEA4-10 gave equivalent results.

The nod-lacZ fusion vectors were introduced into *B. japonicum* strains by standard mating techniques using appropriate selections for the desired transconjugants. Nod gene induction by soybean exudate fractions and potential inducers was assayed in both *B. japonicum* USDA123 and USDA100.

A standard β-galactosidase assay (see Example 2) was used to assay the nod gene induction response to soybean exudate fractions and potential inducer compounds. Initially, an 18–21 hour induction period was allowed before treated *B. japonicum* cultures were assayed for β-galactosidase activity. It was later found (as described in Example 5) that in many cases induction response peaked at considerably earlier times (about 4 hours).

Water extracts of soybean seedlings were found to have some nod gene inducing activity. Methanolic extracts of seedlings, however, had stronger activity, presumably due to the presence of higher concentrations of specific inducer molecules. The methanolic soybean extract or exudate was fractionated as described in Example 3. An initial ether extraction of the exudate removed ether soluble materials (fraction II). The remaining water-soluble portion was hydrolyzed in acid and the resulting hydrolysate was extracted with ether (fraction V). Inducing components of exudate were found to be concentrated in fractions II and V, which by HPLC analysis coupled to nodulation induction assays of HPLC separated fractions, were found to contain only two major components that were nodulation gene inducers (Table 1). These components were identified by standard analytical methods to be the isoflavones daidzein and genistein. Other minor components of fraction v also had some nod gene inducing activity, but have not as yet been identified.

Hydrolysis of soybean exudate significantly enhances its nod gene inducing activity. Flavonoids, including isoflavones, are often present in plants in glycosylated forms. Hydrolysis of the exudate is presumed to deglycosylate the isoflavones and/or flavones present. Aglucon isoflavones appear to be more active inducers of nodulation genes than their glycosylated derivatives.

Figure 3:
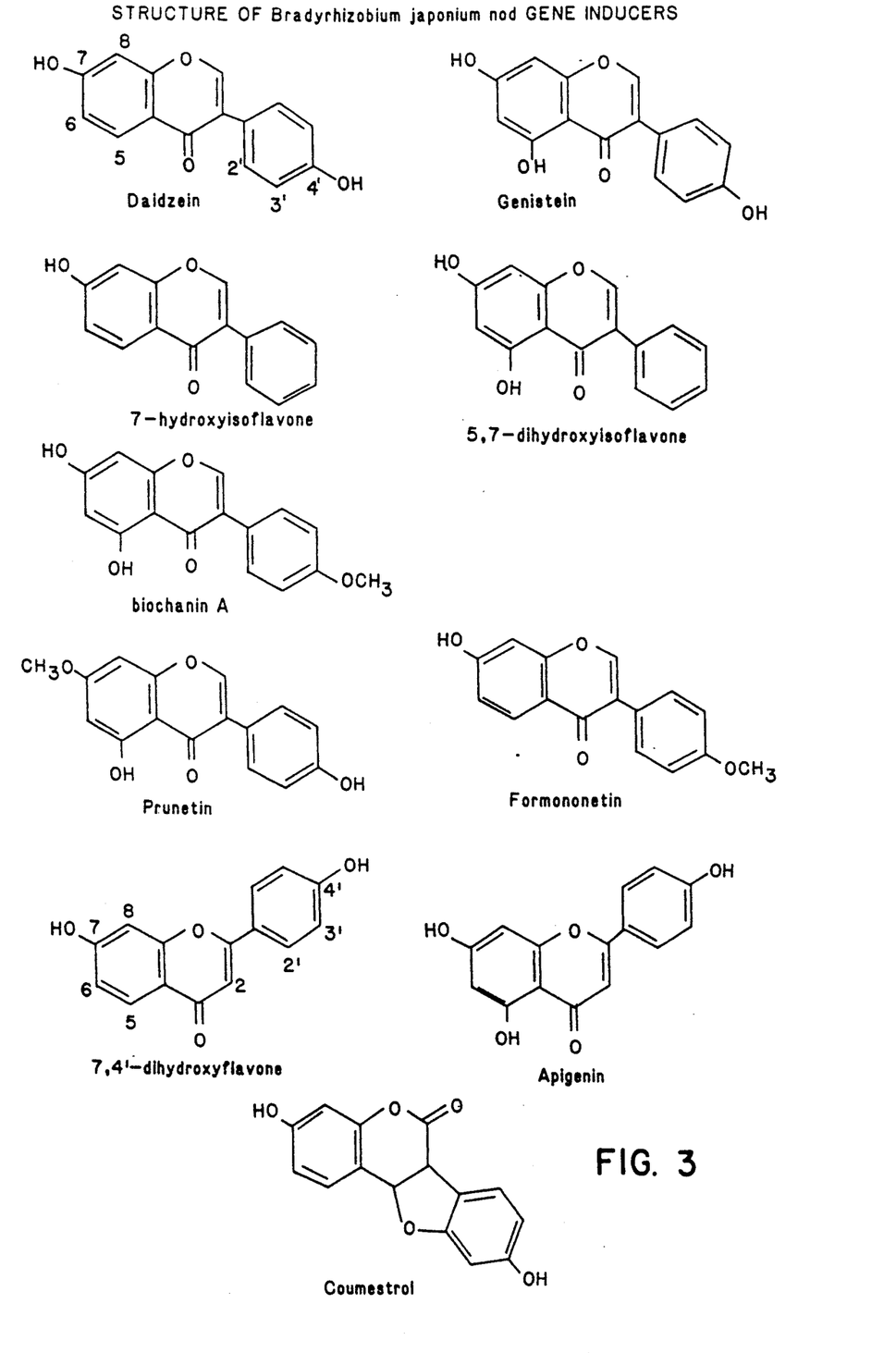
FIG. 3 provides the chemical structure of representative B. japonicum nod gene inducers and weak inducers.

Several isoflavones, flavones and related compounds were assayed for nodulation inducing activity, as summarized in Table 2. Inducing compounds include both isoflavones (daidzein, genistein, 7-hydroxyisoflavone, 5,7-dihydroxyisoflavone, biochanin A and formononetin), flavones (DHF, apigenin) as well as kaempferol (a flavonol) and coumestrol (see FIG. 3 for representative structures). Of the inducers identified, daidzein, genistein and kaempferol had previously been identified as antagonists of Rhizobium nodulation gene induction, at least in *R. leguminosarum* (Firmin et al., 1986). In contrast, DHF and apigenin had been identified as *Rhizobium* nod gene inducers (Zaat et al., 1987; Peters et al., 1986; and Firmin et al., 1986). The specific *B. japonicum* nod gene inducers are not predictable from those of Rhizobium species. Unlike those of Rhizobium species, *B. japonicum* nod genes are induced by compounds having either a flavone or isoflavone ring structure. Inducers of *Rhizobium* nod genes are confined to compounds having a flavone ring structure.

A few structural generalizations for *B. japonicum* nod gene inducers can be made based on the results in Table 2. Both flavones and isoflavones are active. In isoflavones, hydroxylation on the B ring (see FIG. 3) is not essential for activity. In some isoflavone methylation at the 7 or 4' position can decrease induction activity. The structural requirements for activity of isoflavones are different than those of flavones, for example chrysin is inactive while 5,7-dihydroxyisoflavone is active.

Figure 4:
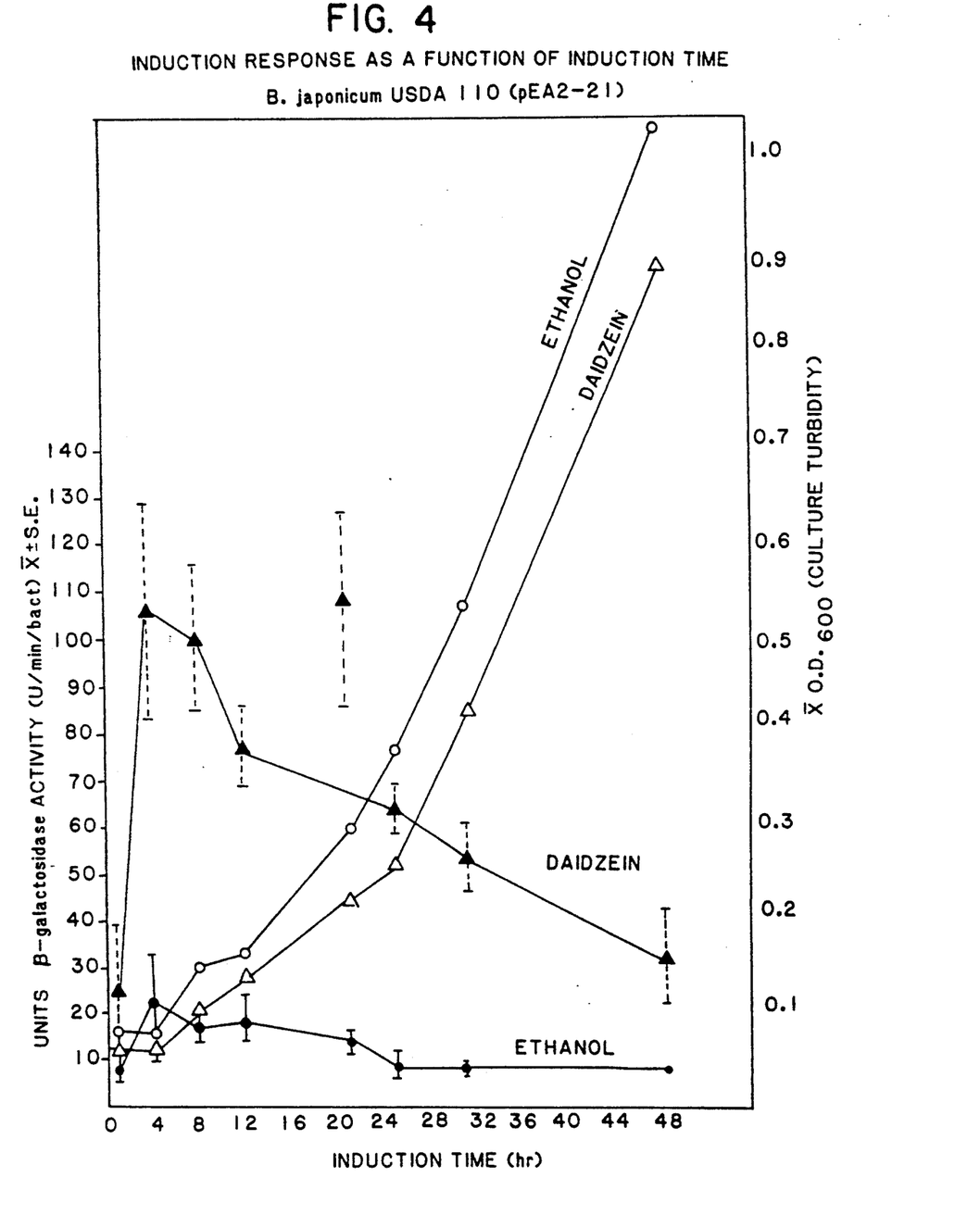
FIG. 4 is a graph of B. japonicum nod gene induction (units $\beta$-galactosidase activity) as a function of induction time (0–48 hours) in the presence of the inducer daidzein. The experiment was performed as in Example 5, with B. japonicum 110 (pEA2-21) adding 5 $\mu$M daidzein at time zero. $\beta$-galactosidase activity induced in response to daidzein is indicated by solid triangles (▲), while the ethanol control is indicated by solid circles (●). The data in the graph are the mean ± standard error of three replicates. Growth curves of *B. japonicum* USDA 110 (pEA2-21) in the presence of daidzein and ethanol (control) are also included. Cell turbidity is measured as optical density at 600 nm (O.D. 600).

An induction time of about 4 hours was required for observation of maximal nod gene induction in exponentially growing *B. japonicum* culture, see FIG. 4. At longer incubation times of bacteria-inducer mixtures, nod gene induction apparently decreases. It is believed that metabolism or inactivation of the inducer by the bacteria occurs and that after about 4 hours the concentration of the inducer drops enough to cause the observed effect in induction response. Different inducers are likely to be metabolized on inactivated more rapidly by *B. japonicum* cultures. In certain applications, as in inoculating compositions, it will be preferred to choose an inducer that is more stable to such effects. The kinetics of nod gene induction may also be affected by the rate of bacterial uptake of the inducer molecule. If uptake is limiting the rate of nodulation induction, culture additives which increase permeability of the cells or enhance solubility of an inducer may lead to rate enhancements.

Induction response as a function of inducer concentration was determined for daidzein, genistein, 4',7-dihdroxyflavone (DHF) and apigenin. Genistein displays induction activity at concentrations down to about 0.1 μM. Daidzein and apigenin display activity down to concentrations between 0.1 to 0.25 μM, while DHF is effective down to concentrations between 0.25 to 0.5 μM.

By analogy with Rhizobium nodulation gene induction, antagonists of *B. japonicum* are likely to exist. Antagonists of *B. japonicum* can include some of the non-inducer molecules identified int he present work. Antagonist activity of a potential antagonist can be identified in nodulation gene induction assays be measuring inhibition of nod gene induction of a known inducer by the potential antagonist (see, for example, Firmin et al., 1986).

Expression of β-galactosidase enzyme activity by nod-lac fusions reflects the regulation of the nodulation genes. β-galactosidase is readily assayed by well known methods including colorimetric assays in which chromogenic substrate such as 5-bromo-4-chloro-3-indolyl-β-D-galactoside (X-gal) or o-nitrophenyl-β-D-galactoside (ONPG) are cleaved to produce blue or yellow colored products, respectively.

Bradyrhizobium strains, particularly *B. japonicum*, which contain nod-lacZ insertions into those nodulation genes which are induced by soybean exudate, for example the nodC fusions of pEA2-21 or pEA4-10, can be employed in combination with well-known assays for β-galactosidase to test substances for the ability to induce nodulation gene. Such assays are applicable to testing of plant exudates, extracts, purified fractions from exudates or extracts, as well as individual molecules prepared by purification from extracts or by synthetic methods for nodulation gene-inducing activity.

Such assays are also applicable to the determination of effective concentration ranges of inducers and for the identification of nodulation induction antagonists.

A number of molecules structurally related to the nodulation gene-inducing flavonoids identified herein are readily available either from commercial sources or can be synthesized by published methods. For synthesis of substituted flavones in particular, see for example, Gaydou and Branchini (1978) Bull. Soc. Chim. France 2:43-44; and Gripenberg (1962) in *The Chemistry of Flavonoid Compounds* Geussman (ed.) Pergamon Press, Oxford. Those of ordinary skill in the art employing the descriptions and nodulation induction assays provided can, without undue experimentation, identify isoflavone and flavone inducers of *Bradyrhizobium japonicum* nodulation genes equivalent to those identified in the present invention.

Kosslak and Bohlool (1984) Plant Physiol 75:125-130 had reported that delayed inoculation of a second side of a soybean split root by 96 hours resulted in significant suppression of nodulation on this second side. Similar results have been found in split-roof experiments of clover inoculated with *R. trifolii* ANU843 (Rolfe et al. 1986) except that a 72 hour delay of inoculation was sufficient to induce suppression. These results suggest that a delay in initiation of nodulation results in a significant competitive disadvantage for the delayed nodulator.

Pretreatment of inoculant strains with nodulation inducers can lead to early initiation of nodulation providing a competitive advantage to inoculant bacteria over the nodulating bacteria present in the rhizosphere.

A primary use of the nodulation inducer compounds of the present invention is in the inoculation of soybeans to effect early initiation of nodulation and thereby enhance the competitiveness of the inoculant strain with respect to the indigenous soil *B. japonicum* population. An inoculating composition can be prepared by combining an effective amount of a nodulation gene inducer of the present invention with a selected strain of *B. japonicum*. Alternatively, a nodulation inducing composition containing an effective amount of a nodulation gene-inducing factor in a suitable concentration of a carrier can be applied to or in the vicinity of an inoculated seed prior to, simultaneously with, or after sowing of the seed. The amount of a particular inducer that is effective for nod gene induction can be determined without undue experimentation.

Using such assays, genistein has been found to induce nod gene expression at concentrations as low as about 0.1 μM. Daidzein and apigenin induce at concentrations as low as 0.1 to 0.25 μM and DHF as low as 0.25 to 0.5 μM. Toxicity toward *B. japonicum* or soybean plants or cell inhibition by an inducer molecule defines the upper limit of its effective concentration range. As a practical matter, the useful upper limit may be determined by the solubility of the inducer in a carrier or diluent.

It is contemplated that nodulation inducing compositions and inoculating compositions of the present invention can contain combinations of two or more inducer compounds. In such cases the inducers must be present in concentrations such that the combination of inducers is effective for nodulation induction. The induction of combination of inducers is readily assayed employing the nodulation induction assays of Example 2.

As will be appreciated by those in the art, nodulation inducing compositions and inoculating compositions of the present invention must be substantially free of antagonists of nodulation induction.

Direct or indirect methods of soybean inoculation can be employed. During direct inoculation the bacterium is applied directly to the seed prior to sowing. This can most simply be accomplished by spraying the seed with or dipping the seed into a liquid culture containing a desired Bradyrhizobium strain and a nodulation gene inducer. A preferred method of direct inoculation is pelleting of the seed with an inoculating composition containing a Rhizobium strain and a nodulation gene-inducing factor. Generally, the bacterium is applied to a carrier material and a pellet is formed with the carrier surrounding the seed. Many diverse carriers are known in the art and include, among others, peat, soil, calcium carbonate, dolomite, gypsum, clay minerals, phosphates, titanium dioxide, humus and activated charcoal. Any agriculturally suitable material can be employed. An adhesive material is often included in such a pellet to insure that the carrrier remains in contact with the seed. Again, many acceptable adhesives are known including, among others, synthetic glues, vegetable glues, gelatin and sugars. In general, the carrier and any adhesive used are chosen to insure viability of the inoculant strain and retention of activity of nodulation gene-inducing factor. Pelleted inoculated seed containing an inducing factor can be directly sown into the field. Alternatively, a conventionally prepared inoculated seed or seed pellet containing the desired strain can be contacted with an inducing composition containing an effective amount of a nodulation gene inducer before, with or after sowing of the inoculated seed. Those skilled in the art are aware that the concentration of inducer that is required for induction can be effected by the carriers employed. For example, certain carriers typically used in inoculating compositions may adsorb inducer molecules making them more or less available for induction by bacteria.

During indirect inoculation an inoculating composition of the present invention containing an inoculant strain and an effective concentration of a nodulation gene inducer is introduced in the vicinity of the seed at the time of sowing. The inoculating composition is in a suitable carrier material to aid in application. The carrier can be a solid or liquid material but must be non-toxic to plant and bacteria, as well as chemically inert to nod gene inducer. Examples of carriers include, among others, aqueous solutions with or without buffering agents; peat and other materials cited above as potential carriers. Bacterial nutrients may also be included in such carriers.

The following references provide a description of basic techniques in the art of agricultural inoculation: Brockwell (1962) Aust. J. Agr. Res. 13:638; Bergersen et al. (1958) J. Aust. Inst. Agric. Sci. 24:158; Hastings et al. (1962) N. Z. J. Agr. 104:330; Fraser (1966) J. App. Bacteriol. 29:587; Schiel et al. (1970) Rev. Invest. Agropec. Ser. 2 7:2349; Iswaran et al. (1971) Zentralbl. Bakteriol. Parasitenk. Infektionskr. Abt. II 126:43,45.

Another use of the nodulation gene inducers of the present invention is for selective induction in *B. japonicum* of genes containing a soybean exudate-inducible promoter and a structural gene under its control. Expression of a gene containing a soybean-inducible promoter, for example the nodABC promoter of *B. japonicum* USDA 123 or 110, can be activated by addition of an effective amount of a nodulation gene inducer to a culture of the bacteria which contain the gene and in which the soybean-inducible promoter is inducible. It is well known in the art that bacterial growth conditions (pH, nutrients, etc.) and bacterial growth stage can affect inducibility of regulated promoters. Certain promoters can only be induced at certain growth stages. Inducibility of a soybean exudate inducible promoter as a function of culture conditions or bacterial growth state can be ascertained by methods analogous to those of Example 5.

Expression of genes which contain legume inducible promoters including heterologous or chimeric genes and non-gene fusions can be selectively controlled by application of nodulation inducers and nodulation inducing compositions. Nod-gene fusions are prepared by insertion of a structural gene into a nodulation gene as exemplified herein with pEA2-21 or pEA4-10. Soybean exudate inducible chimeric genes are prepared by joining or ligating a heterologous structural gene to a soybean exudate inducible promoter, particularly a *B. japonicum* nodulation gene promoter. As is well known in the art, the heterologous gene must be inserted or ligated in the correct orientation (vide infra) with respect to the promoter to be placed under its regulatory control.

In principle, any commercially useful gene product originating from either prokaryotic or eukaryotic genes can be selectively expressed by addition of a nodulation gene-inducing factor. Limitations well known in the art include gene products that are toxic to the production bacterium. For eukaryotic genes, no introns must be present in the gene coding region; if introns are present in the chromosomal gene, a cDNA copy of the structural gene can be employed in constructions. Structural gene products whose expression can be controlled using this method include, among others, *Bacillus thuringiensis* insect toxin, the sweet plant protein thaumatin and metallothienin (Karin, M. and R. I. Richards (1982) Nucleic Acids Res. 10:3165; Wong et al. (1983) J. Biol. Chem. 258:160; Edens et al. (1982) Gene 18:1–12). An important aspect of the method is that a source of nodD gene product must be present, in addition to a nodulation gene-inducing factor, in order to activate legume exudate-inducible promoters. The bacterium must contain a functional nodD gene. The nodD-lacZ fusions of the present invention are examples of DNA constructions which meet this requirement. Alternatively, it may be possible to provide an exogenous supply of appropriate nodD gene product.

Those of ordinary skill in the art will appreciate that the invention described herein and the method of isolation and assay methods specifically described are susceptible to variations and modifications other than as specifically described. It is to be understood that the invention includes all such variations and modifications which fall within its spirit and scope. The following examples are provided for illustrative purpose only and are not intended to limit the scope of the invention.

EXAMPLE 1

Construction of *B. japonicum* nodC-lacZ fusions

Clones and subclones containing the nod region of *B. japonicum* USDA 123 were obtained as described previously (Appelbaum et al., U.S. patent application Ser. No. 875,297, filed Jun. 17, 1986). Briefly, a *B. japonicum* USDA 123 cosmid gene bank was prepared. Total genomic USDA 123 DNA was prepared as in Scott, 1981 (J. Mol. Appl. Genet. 1:71–81), and partially digested with EcoRI. Digested DNA was then fractionated on a sucrose gradient to isolate DNA fragments ranging in size from 12–50 kb. These DNA fragments were ligated to EcoRI digested pLAFR1 (Freedman et al. (1982) Gene 18: 289–296). The ligated DNA was packaged into phage heads using conventional techniques and introduced into *E. coli* strain HB101. A total of 6200 cosmids were saved for screening. This cosmid bank of *B. japonicum* DNA was screened for cosmids capable of hybridizing to a 2 kb BamHI/HindIII fragment of pRmSL42 that contains the nodAB and C sequences of *R. meliloti* (Egelhoff et al. 1985). One strongly hybridizing cosmid was found which contained a 1.6 kb EcoRI fragment that was subsequently shown to contain *B. japonicum* nod A and B sequences. The insert of the selected cosmid was then employed to rescreen the cosmid bank for larger inserts. One cosmid, designated pEA71-1A, selected by this screen was picked, repurified and the approximately 30 kb cosmid insert was subjected to restriction analysis. Digestion of this large fragment with EcoRI resulted in several EcoRI subfragments, including a 1.6 kb fragment which hybridized to the 1.6 kb EcoRI fragment obtained by direct screening (vide supra) and a 3.6 kb fragment which hybridized to a 3.0 kb nodD probe which contained the nodD-r2 gene of *R. fredii* USDA 191 (Appelbaum U.S. application Ser. No. 763,934, filed Aug. 7, 1985, now abandoned). Southern blot analysis using several restriction enzymes indicated that these two fragments were adjacent to each other in the large cosmid insert. The nod region of *B. japonicum* USDA 123 is contained in this cosmid insert. The positions and orientations of nod genes within this region were confirmed by DNA sequencing and are shown in FIG. 1 in which the regions sequenced are noted.

A 4.3 kb HindIII fragment of the nod region of USDA 123 which contained nodD, the promoter regions of nodD and nodA, including nod-box, nodA, nodB and the amino terminal end of nodC was subcloned into the unique HindIII site of the vector pIC19R (Marsh et al. (1984) Gene 32:481–485). In this vector, the HindIII site is flanked by a unique BamHI site on one side and a BglII site on the other side. Clones containing both orientations of the insert were obtained (see FIG. 2). In clone pEA-H17-4, the insert is flanked by a unique BamHI site on the nodD side of the insert and a BglII site on the nodC side of the insert. Clone pEA-H17-2 contains the insert in the opposite orientation, with a BglII site on the nodD side of the insert and BamHI site on the nodC side.

pEA-H17-4 and pEA-H17-2 were each digested with BamHI and BglII restriction endonucleases, and the resulting 4.3 kb fragments containing the nod genes were cloned into BamHI digested pGD926 (Ditta et al. (1985) Plasmid 13:149–153). The 4.3 fragment from pEA-H17-2 yielded a clone pEA2-21 in which nodC is joined in frame to lacZ by a HindIII-BamHI linker sequence which encodes 7 amino acids. The fragment from pEA-H17-4 yielded a clone, pEA-10 in which nodC is joined in frame to lacZ by a HindII-BglII/-BamHI linker sequence that encodes 6 new amino acids.

Plasmids pEA2-21 and pEA4-10 have behaved identically in all nod/lacZ expression assays preformed. Each construction has certain advantages for further genetic manipulations. The unique BamHI site in the nodC-lacZ intergenic linker in pEA2-21 is a useful site for the insertion of other genes in order to place them under the control of the nodA promoter. The unique BamHI site downstream of nodD in pEA4-10 is a useful site for insertion of the second nodD gene of $B. japonicum$ and can also be used for insertion of heterologous genes in order to place them under the control of the nodD promoter.

Plasmids pEA2-21 and pEA-10 were routinely propagated in $E. coli$ MC1061. The plasmids were mobilized into $B. japonicum$ by standard crosses in which a helper plasmid, pRK2013 (Ditta et al. (1980) Proc. Natl. Acad. Sci. U.S.A. 77:7347–7351) provides transfer functions. Each mating consisted of a mixture of three strains: the donor strain, $E. coli$ MC1061 containing either pEA2-21 or pEA-10, the helper strain, $E. coli$ K802 containing pRK2013, and the Bradyrhizobium recipient strain. Spontaneous spectinomycin (spc) resistant mutants of the various Bradyrhizobium strains were used as recipient strains. Both nod-lac fusion plasmids also carry tetracycline resistance. The mating mixtures were incubated in non-selective media to allow mating to occur after which they were plated on selective media containing tetracycline (75 mg/l) and spectinomycin (250 mg/l). Colonies that grow on the selective media should be transconjugant Bradyrhizobium strains which carry the nod-lac fusion plasmid. Transconjugants were selected, repurified and then typed by standard serological techniques using strain-specific antisera that distinguish the rhizobia from each other and from $E. coli$.

Induction of expression of the USDA123 nodC-lacZ fusions was examined in the $B. japonicum$ strains USDA123 spc and USDA110 spc which are spontaneous spc resistant mutants of the wild-type strains. $Bradyrhizobium japonicum$ USDA123 spc containing pEA2-21 and $B. japonicum$ EA2-61 (nod-deletion mutant) containing pEA2-21 have been placed on deposit with the Northern Regional Research Laboratory (NRRL), 1815 North University Street, Peoria, Ill. 61604, and given the accession numbers B-18193 and B-18192, respectively.

EXAMPLE 2

Assay for Induction of nod Genes

Exponentially growing cultures of strains containing pEA2-21 or pEA4-10 were incubated with soybean root exudate preparations or fractions, see Table 1, or with ethanol solutions of flavones, isoflavones and related compounds, see Table 2. In the case of addition of ethanol solutions of individual compounds, the final concentration of ethanol in the culture was always less than 2% (v/v) and an equivalent amount of ethanol was included with controls. Samples and controls were incubated at 28° C., after which aliquots were taken for β-galactosidase assay and measurement of culture turbidity (O.D. 600).

The standard o-nitrophenyl-β-D-galactoside (ONPG) β-galactosidase assay of Miller (1972) *Experiments in Molecular Genetics,* Cold Spring Harbor Press, Cold Spring Harbor, N.Y. was used. Samples were treated with toluene to permeabilize cells, incubated with ONPG for up to two hours after which the absorbence of the sample at 420 nm was measured. β-galactosidase activity is expressed in "Jiller units" (U) which are defined by the equation:

$$U = 1000 \times O.D.\ 420 / V \times T \times O.D.\ 600$$

where O.D. 420 is the absorbence at 420 nm, O.D. 600 is the absorbence at 600 nm (culture turbidity), V is the volume of culture mixed with buffer (total sample volume is 1 ml) and T is the time of incubation with ONPG in minutes.

EXAMPLE 3

Identification of soybean exudate components that induce nod-lac fusions in strains of Bradyrhizobium japonicum Seeds of Glycine max cv. Williams were surface sterilized for 10 minutes in commercial bleach, rinsed once with sterile distilled water, immersed for 5 minutes in 1% (v/v) HCl and finally rinsed six times with sterile distilled water. Sterilized seeds were germinated by culturing on 1% (wt/v) yeast extract-mannitol agar for three days at 27° C. For preparation of plant exudate, 200 g of seeds were germinated. Three day old seedlings were extracted for 24 hr. in 300 ml of a 9:1 (v/v) mixture of methanol/water followed by a second extraction (24 hr) in 300 ml of a 1:1 (v/v) methanol/water mixture. The methanolic extracts were combined and the solvent was removed under vacuum. The resulting residue (7.8 g) was dissolved in water (200 ml) and the solution was filter sterilized using a 0.22 micron cellulose acetate filter. This material is whole soybean exudate and is designated fraction I.

A portion (150 ml) of fraction I was extracted (3×) with anhydrous ethyl ether and dried. The ether extract was concentrated to dryness under vacuum. The resulting residue (40 mg) was dissolved in 100 ml of a 1:99 (v/v) ethanol:water solution, filter sterilized and the pH was adjusted to 6.5 for biological assays. This ether soluble fraction was designated fraction II.

The remaining water-soluble fraction (ether extracted fraction I) was concentrated to dryness under vacuum and the residue (6.16 g) was dissolved in 150 ml of water and the resulting aqueous solution was filter sterilized. This fraction was designated fraction III.

A portion of fraction III (73 ml) was hydrolyzed in acid (6% v/v concentrated HCl) for 1 hr at reflux. The resultant hydrolysate was extracted with ether (5×). The ether extract of the hydrolysate was concentrated to dryness under vacuum and the resultant residue (100 mg) was dissolved in HPLC grade methanol. This material was designated fraction V. For use in bioassays, methanol was removed under vacuum for 1 ml aliquots of fraction V and the residue was then dissolved in 1 ml of punctilious ethanol.

The water-soluble, ether extracted hydrolysate, was concentrated to dryness under vacuum, the residue was dissolved in water, the pH adjusted to 6.5 and the solution was filter sterilized. This material was designated fraction IV.

Fractions I-V were assayed as described in Example 2 for nod gene induction activity in both *B. japonicum* USDA 110 and 123. In addition, 10, 100 and in most cases 1000 fold dilutions of each fraction were assayed. The results of these assays are shown in Table 1. All fractions displayed nod gene inducing activity; however, when induction as measured in Units of $\beta$-galactosidase activity was adjusted for the concentration of the fraction (mg residue/ml), two fractions, II and V, display much higher inducing activity/mg residue. Fraction II and Fraction V were found to be from 1000 to 10,000 times more active on a weight basis than any of the other fractions.

Non-diluted fraction II and V and the 1:10 dilution of fraction II were found to inhibit growth of USDA 110 or USDA 123. In all cases, the induction response appeared to saturate at higher concentrations with stronger induction responses observed with increasing dilution of a fraction. This effect may result from saturation of the induction response as a function of inducer concentration or may be due fully or in part to bacterial growth inhibition.

Each fraction was separated into components using conventional high pressure liquid chromatography (HPLC) methods on a C-18 reverse phase column employing a methanol/H20 gradient. Subfractions corresponding approximately to each major HPLC peak were collected, chromatographed a second time and recollected, after which solvents were removed under vacuum and the residues were weighed and dissolved in ethanol. The nod gene inducing activity of the HPLC separated components of each fraction was assayed. The majority of the activity in fractions I, II and V was found to reside in the same two components. These components have been identified as daidzein and genistein by mass spectral and NMR analysis and by comparison of the chromatographic properties (thin layer and HPLC) and UV spectra of the isolated components with those of the authentic compounds. The two purified components of exudate, that were identified as daidzein and genistein, display nod gene induction activity equivalent to commercially available daidzein and genistein.

Two minor components in fraction V were found to have somewhat weaker nod gene inducing activity than daidzein or genistein (10–30 fold less on a weight basis). These components have not as yet been identified.

EXAMPLE 4

Induction of Nod-lac fusions by flavones, isoflavones and relate compounds

A variety of isoflavones, flavones and related compounds were assayed for nod gene induction activity in both USDA 110 and USDA 123 containing the nod-lac fusions described in Example 1 using the method described in Example 2. Most compounds tested were obtained from commercial sources and were used without further purification. Samples of 7hydroxyisoflavone, 5,7-dihydroxyflavone, 3',4',7-trihydroxyisoflavone and 3',4',5',7-tetrahydroxyisoflavone (Baptigenin) were provided by Dr. John Norris (University of Texas, Austin). The procedure of Gaydou and Bianchini (1978) Bull. Soc. Chimi. France 2:43 was used to synthesize 4',7-dihydroxyflavone.

Table 2presents representative results of nod gene induction assays for individual compounds. Included in this Table are assays with both USDA 123 and USDA 110 at two induction times. In each case, the potential inducer was added to the culture at a concentration of 5 $\mu$M at time zero. Induction response was measured as $\beta$-galactosidase activity as defined in Example 2. Since the bacteria continue to grow during the induction period, the data taken at 4 and 21 hr. represent measurements made on bacterial cultures in different growth stages. The data in Table 2 are the mean of three replicates ($\pm$standard deviation). The compounds tested have been assessed qualitatively as inducers (+), weak inducers (w) or non-inducers (−), based on the results in Table 2. A positive induction response corresponds to $\beta$-galactosidase activity at least 4-fold higher than background. A weak response corresponds to enzyme activity at least 2-fold but less than 4-fold over background. A negative response is enzyme activity less than 2-fold over background. A molecule was assessed as an inducer if a positive induction response was observed at either of the induction time points. Weak inducers were assessed in a similar way.

Daidzein, genistein, 7-hydroxyisoflavone, 5,7-dihydroxyisoflavone, biochanin A, 4',7-dihydroxyflavone and apigenin induced a positive response with both strains. Formononetin induced a positive response with USDA 110 and a weak response with USDA 123. Kaempferol of both strains, while coumestrol was a weak inducer for strain USDA 110. The isoflavones, baptegenin and 3',4',7-trihydroxyisoflavone displayed no nod gene induction response in these experiments. The flavones luteolin, chrysin, naringenin and quercetin did not induce nod gene expression in these experiments. In addition, umbelliferone (results in Table 2) and estrone, $\beta$-estradiol, trigonelline and diethylstilbestrol (results not in Table 2) did not induce nod gene expression when assayed at 5 $\mu$M level.

EXAMPLE 5

Time course of induction as a function of incubation time

Daidzein or other inducers (5 $\mu$M) were added to exponentially growing cultures of *B. japonicum* containing pEA2-21 at time zero. Aliquots of the resulting cell/induction mixture were sampled as a function of incubation time in the presence of the inducer, 0–48 hr, and $\beta$-galactosidase activity and culture turbidity were measured. FIG. 4 presents the results of one such experiment in which *B. japonicum* USDA 110 was incubated with 5 μM daidzein. It should be noted that the bacteria continue to grow during the time course of the experiment and that the β-galactosidase units are normalized for bacterial growth (see Example 2). The growth curve of the bacterial cultures (O.D. 600) is included in FIG. 4. Specific β-galactosidase activity peaks at about four hours and gradually decreases as a function of time. The observed variation in specific enzyme activity is consistent with continued production of β-galactosidase during the first hours of incubation, up until about four hours, after which enzyme production stops. Since bacterial growth continues, the specific activity drops. Although it has not been quantified, there is evidence that the inducer molecules are metabolized or chemically transformed by the bacteria during incubation. In these experiments, it is likely that induction stops because the concentration of inducer molecule in the system drops below the effective level (see Example 6).

EXAMPLE 6

Nod Gene Induction Response as a Function of Inducer Concentration

Induction response as a function of inducer concentration was determined for daidzein, genistein, 4',7-dihydroxyflavone (DHF) and apigenin. Induction assays were performed as described in Example 2, with an induction period of 4 hr. The results are presented in Table 3. In all cases induction saturated at higher inducer concentrations. Genistein displays significant induction activity (i.e. greater than 2-fold background) at concentrations as low as 0.1 μM. Daidzein and apigenin induce significant β-galactosidase activity by concentrations between 0.1 and 0.25 μM. Inducing activity of DHF is not significant until concentrations between 0.25 to 0.5 μM.

TABLE 1

Nod Gene Induction Activity of Soybean Exudate Fractions

| Fraction[2] | β-galactosidase Activity (Normalized Units[1]) Strain: | |
|---|---|---|
| (concentration (mg/l) or dilution) | USDA 110 | USDA 123 |
| I (38.9) | 2 ± 28% | — |
| (1:10) | 14 ± 3% | 24 ± 14% |
| (1:100) | 86 ± 3% | 172 ± 9% |
| (1:1000) | — | 334 ± 14% |
| II (0.398) | inhibited growth | — |
| (1:10) | 1268 ± 7% | inhibited growth |
| (1:100) | 9422 ± 9% | 22,236 ± 11% |
| (1:1000) | — | 50,251 ± 19% |
| III (41.06) | 1 ± 15% | — |
| (1:10) | 12 ± 6% | 24 ± 45% |
| (1:100) | 35 ± 5% | 22 ± 10% |
| (1:1000) | — | 98 ± 20% |
| IV (29.1) | — | — |
| (1:10) | 3 ± 7% | 16 ± 2% |
| (1:100) | 9 ± 12% | 14 ± 20% |
| V (0.28) | inhibited growth | — |
| (1:10) | 1732 ± 7% | 2804 ± 12% |
| (1:100) | 12,679 ± 7% | 47,857 ± 8% |
| (1:1000) | — | 42,857 ± 15% |

[1] β-galactosidase activity was measured as described in Example 2, with an induction time of 18–21 hours. Specific activity (-background) was normalized for fraction concentration in mg/ml to allow comparison of different fractions. The values are the mean ± standard deviation (%) of three replicate samples.
[2] Fractions are as described in Example 3.

TABLE 2

B. japonicum Nod Gene Induction Response

| | Induction Response B. japonicum[1] | | | | | | | |
|---|---|---|---|---|---|---|---|---|
| | USDA 110 | | | | USDA 123 | | | |
| Compounds | 2 hrs | | 4 hrs | | 2 hrs | | 4 hrs | |
| Background | 10 ± 3 | | (9 ± 0) | | 8 ± 5 | | (10 ± 3) | |
| bean Root Exudate (fraction I)[2] | 72 ± 20 | + | (ND) | | 95 ± 13 | + | (ND) | |
| Isoflavones | | | | | | | | |
| Daidzein | 63 ± 6 | + | (51 ± 2) | + | 76 ± 8 | + | (56 + 8) | + |
| Genistein | 67 ± 5 | + | (61 ± 5) | + | 65 ± 2 | + | (76 ± 11) | + |
| 7-hydroxyisoflavone | 56 ± 4 | + | (56 ± 5) | + | 65 ± 2 | + | (12 ± 4) | — |
| 5,7-hydroxyisoflavone | 68 ± 5 | + | (70 ± 5) | + | 110 ± 16 | + | (68 ± 13) | + |
| Baptigenin | 12 ± 1 | — | (ND) | | 11 ± 1 | — | (ND) | |
| 3',4',7-trihydroxyisoflavone | 14 ± 1 | — | (ND) | | 9 ± 1 | — | (ND) | |
| Biochanin A | 37 ± 3 | + | (61 ± 6) | + | 14 ± 2 | — | (51 ± 12) | + |
| Formononetin | 19 ± 5 | — | (35 ± 9) | + | 11 ± 1 | — | (22 ± 4) | w |
| Flavones | | | | | | | | |
| 4',7-dihydroxyflavone | 43 ± 4 | + | (57 ± 4) | + | 30 ± 4 | + | (52 ± 6) | + |
| Apigenin | 21 ± 2 | w | (43 ± 11) | + | 38 ± 12 | + | (68 ± 9) | + |
| Luteolin | 7 ± 1 | — | (14 ± 2) | — | 4 ± 1 | — | (15 ± 1) | — |
| Chrysin | 6 ± 10 | — | (12 ± 1) | — | 7 ± 1 | — | (13 ± 3) | — |
| Flavanone/Flavonols | | | | | | | | |
| Naringenin | 8 ± 10 | — | (12 ± 1) | — | 4 ± 1 | — | (13 ± 3) | — |
| Quercetin | 7 ± 1 | — | (11 ± 1) | — | 4 ± 1 | — | (11 ± 2) | — |
| Kaempferol | 20 ± 2 | w | (18 ± 3) | w | 18 ± 9 | w | (12 ± 1) | — |
| Coumestans | | | | | | | | |
| Coumestrol | 27 ± 4 | w | (22 ± 1) | w | 13 ± 2 | — | (19 ± 3) | — |
| Umbelliferone | 8 ± 1 | — | (10 ± 1) | — | 4 ± 1 | — | (12 ± 1) | — |

[1] In all cases the B. japonicum strain contains the nodC-lacZ fusion plasmid pEA2-21; Induction response is measured as β-galactosidase activity (Example 2); + = activity 4-fold over background; w (weak) = activity at least 2-fold but less than 4-fold over background; — = activity less than 2-fold over background
[2] Preparation of soybean exudate fraction is described in Example 3

TABLE 3

Nod Gene Induction Response as a Function of Inducer Concentration Induction Response[1]

| Concentration (μM) | Daidzein | Genistein | DHF[2] | Apigenin |
|---|---|---|---|---|
| 0 | 11 ± 1 | 20 ± 3 | 11 ± 1 | 20 ± 3 |
| 0.1 | 21 ± 2 | 47 ± 9 | 13 ± 1 | 23 ± 2 |
| 0.25 | 38 ± 3 | 72 ± 4 | 20 ± 4 | 41 ± 8 |
| 0.5 | 42 ± 1 | 78 ± 8 | 26 ± 1 | 54 ± 9 |
| 1.0 | 46 ± 2 | 84 ± 4 | 48 ± 8 | 55 ± 11 |

TABLE 3-continued

Nod Gene Induction Response as
a Function of Inducer Concentration
Induction Response[1]

| Concentration (μM) | Daidzein | Genistein | DHF[2] | Apigenin |
|---|---|---|---|---|
| 2.5 | 53 ± 5 | 83 ± 11 | 76 ± 2 | 80 ± 8 |
| 5.0 | 58 ± 5 | 83 ± 5 | 81 ± 3 | 110 ± 11 |
| 10.0 | 51 ± 2 | 65 ± 7 | 75 ± 5 | 104 ± 1 |

[1]Induction response measured as units of β-galactosidase activity as described in Example 2 with an induction time of 4 hours. The values listed are the mean ± standard deviation of three replicates
[2]DHF = 4,7-dihydroxyflavone

We claim:

1. A soybean inoculating composition which comprises
    (a) a bacterium of the species *Bradyrhizobium japonicum;*
    (b) a nodulation inducing compound which is a flavonoid which induces expression of a nodABC operon of a strain of *Bradyrhizobium japonicum*, said compound being present in a concentration effective for induction of said operon; and
    (c) an agriculturally suitable carrier.

2. The composition of claim 1 wherein said nodulation inducing compound is effective for induction at a concentration less than 1.0 μM.

3. The composition of claim 1 wherein said nodulation inducing compound is effective for induction at a concentration of 0.1 μM.

4. The composition of claim 1 wherein said nodulation inducing compound has an isoflavone ring structure.

5. The composition of claim 1 wherein said strain of *Bradyrhizobium japonicum* is *Bradyrhizobium japonicum* USDA 123.

6. The composition of claim 1 wherein said strain of *Bradyrhizobium japonicum* is *Bradyrhizobium japonicum* USDA 110.

7. A method of inoculating a soybean comprising the step of applying in the vicinity of a seed of said soybean the nodulation inducing composition of claim 1.

8. The method of claim 7 wherein said strain of *Bradyrhizobium japonicum* is *Bradyrhizobium japonicum* USDA 110.

9. The method of claim 7 wherein said strain of *Bradyrhizobium japonicum* is *Bradyrhizobium japonicum* USDA 110.

10. A soybean inoculating composition which comprises
    a) a bacterium of the species *Bradyrhizobium japonicum;*
    b) a nodulation inducing compound which is a flavonoid which induces expression of a nodABC operon of a strain of *Bradyrhizobium japonicum*, said compound being present in a concentration effective for induction of said operon; and
    c) an agriculturally suitable carrier; wherein said nodulation inducing compound is selected from the group consisting of daidzein, genistein, 7-hydroxyisoflavone, 5,7-dihydroxyisoflavone, biochanin A, formononetin, 4',7-dihydroxyflavone, apigenin, kaempferol and coumestrol.

11. The composition of claim 10 wherein said nodulation inducing compound is selected from the group consisting of daidzein, genistein, 7-hydroxyisoflavone, 5,7-dihydroxyisoflavone, biochanin A and formononetin.

12. The composition of claim 10 wherein said nodulation inducing compound is selected from the group consisting of 4',7-dihydroxyflavone, apigenin and kaempferol.

13. The composition of claim 10 wherein said nodulation inducing compound is kaempferol.

14. The composition of claim 10 wherein said nodulating inducing compound is coumestrol.

15. A method of inoculating a soybean comprising the step of applying in the vicinity of a seed of said soybean a nodulation inducing composition, said nodulation inducing composition comprising
    a) a bacterium of the species *Bradyrhizobium japonicum;*
    b) a nodulation inducing compound which is a flavonoid which induces expression of a nodABC operon of a strain of *Bradyrhizobium japonicum*, said compound being present in a concentration effective for induction of said operon; and
    c) an agriculturally suitable carrier; wherein said nodulation inducing compound is selected from the group consisting of daidzein, genistein, 7-hydroxyisoflavone, 5,7-dihydroxyisoflavone, biochanin A, formononetin, 4',7-dihydroxyflavone, apigenin, kaempferol and coumestrol.

16. The method of claim 15 wherein said nodulation inducing compound is selected from the group consisting of daidzein, genistein, 7-hydroxyisoflavone, 5,7-dihydroxyisoflavone, biochanin A, and formononetin.

17. The method of claim 15 wherein said nodulation inducing compound is selected from the group consisting of daidzein, genistein, 7-hydroxyisoflavone, 5,7-dihydroxyisoflavone and biochanin A.

18. The method of claim 15 wherein said nodulation inducing compound is selected from the group consisting of 4',7-dihydroxyflavone, apigenin and kaempferol.

19. The method of claim 15 wherein said nodulation inducing compound is kaempferol.

20. The method of claim 15 wherein said nodulation inducing compound is coumestrol.

* * * * *